US00PP26533P3

(12) United States Plant Patent
Olesen

(10) Patent No.: US PP26,533 P3
(45) Date of Patent: Mar. 29, 2016

(54) GROUND COVER ROSE PLANT NAMED 'POULTC018'

(50) Latin Name: ***Rosa* hybrid**
Varietal Denomination: Poultc018

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 234 days.

(21) Appl. No.: 13/986,911

(22) Filed: Jun. 14, 2013

(65) Prior Publication Data

US 2014/0373200 P1 Dec. 18, 2014

(51) Int. Cl.
*A01H 5/00* (2006.01)
*A01H 5/02* (2006.01)

(52) U.S. Cl.
USPC ..... Plt./108
CPC ..... *A01H 5/0222* (2013.01)

(58) Field of Classification Search
USPC ..... Plt./108
See application file for complete search history.

(56) References Cited

PUBLICATIONS

Pagode Perfection by Poulsen 2012-2013.*

* cited by examiner

*Primary Examiner* — Annette Para

(57) ABSTRACT

A new garden rose plant of the Ground Cover class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poultc018'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poultc018', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant red flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poultc018' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poultc018' was selected in the spring of 2008 by the inventor as a single plant from the progeny of the aforementioned hybridization.

Asexual reproduction of 'Poultc018' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poultc018' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc018'.

Specifically illustrated in FIG. 1 are flowers in parts, stems and leaves.

DETAILED DESCRIPTION OF THE VARIETY

Figure 1:
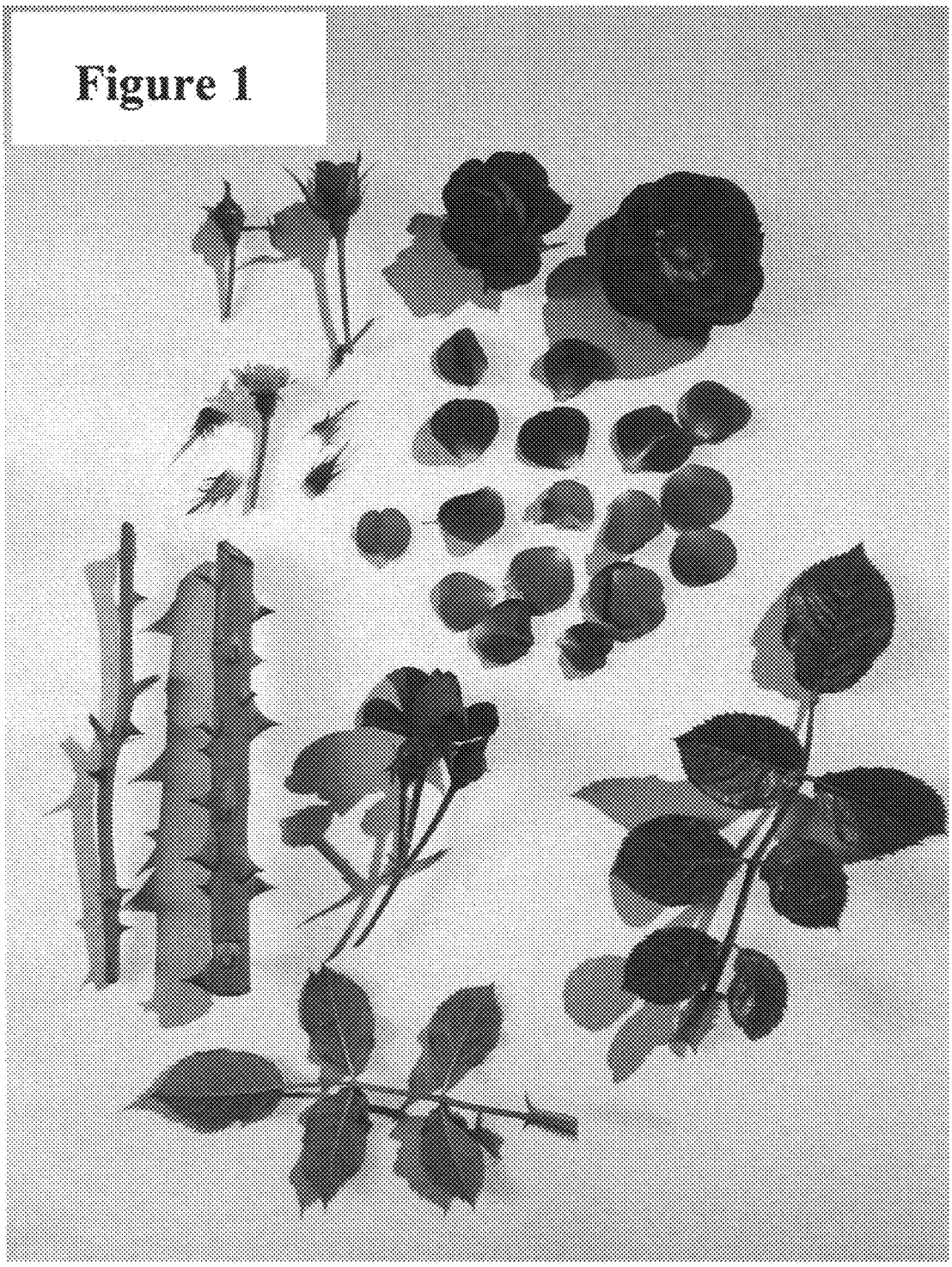
Figure 2:
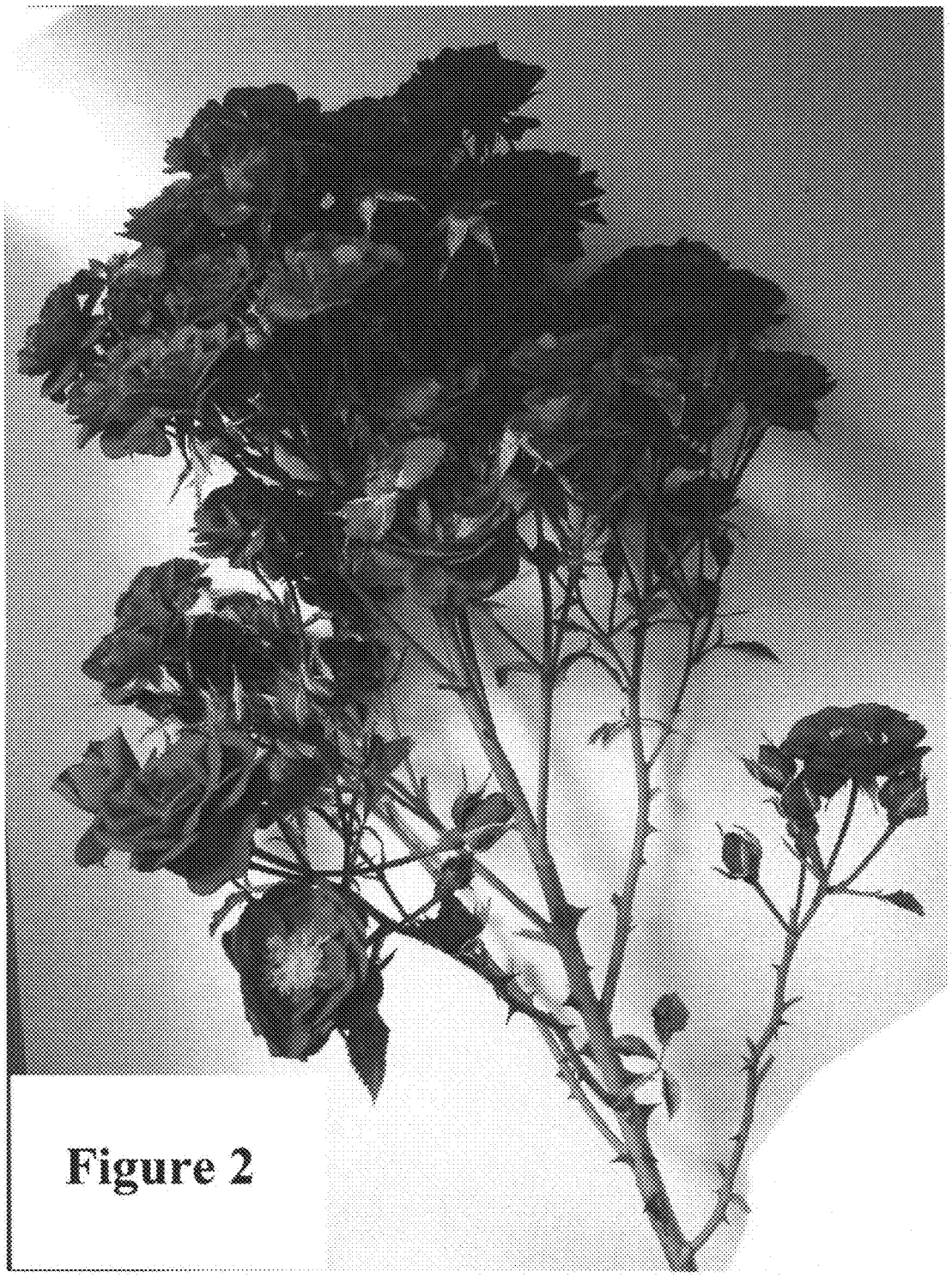
FIG. 2 a flowering branch.

The following is a description of 'Poultc018', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poultc011', U.S. Plant Pat. No. 18,488 are compared to 'Poultc018' in Chart 1.

CHART 1

| | 'Poultc018' | 'Poultc011' |
|---|---|---|
| Petal Count | 20 petals | 12 petals with 2 petaloids |
| Flower Diameter | 50 mm | 55 mm |
| General Tonality of Flower Color | Red Group 46A | Red Group 45B to Red Group 46B |

Flower and Flower Bud

Blooming habit: Continuous.

Flower bud:

*Size*.—Upon opening, 15 mm in length from base of receptacle to end of bud. Bud diameter is 12 mm.

*Bud form*.—Urceolate.

*Bud color*.—As sepals divide Red Group 46A and Greyed-Purple Group 185A.

*Sepal inner surface*.—Color: Greyed-Purple Group 184A. Surface: Smooth, moderately pubescent.

*Sepal outer surface*.—Color: Yellow-Green Group 144A with strong intonations of Greyed-Purple Group 183A. Texture: Smooth.

*Sepal shape*.—Apex: Cirrhose. Base: Flat at union with receptacle.

*Sepal margin*.—Margins have strong foliaceous appendages on three of the five sepals.

*Sepal size*.—18 mm long by 7 mm wide.

*Receptacle*.—Texture: Smooth. Size: 5 mm in height by 5 mm wide. Color: Yellow-Green Group 144A. Strong anthocyanic pigments the color of Greyed-Purple Group 183A observed. Shape: Elliptical.

*Pedicel*.—Surface: Rough with many stipitate glands. Length: 30 mm. Diameter: 2 mm on average. Color: Yellow-Green Group 144C. Anthocyanic pigments the color of Greyed-Purple Group 184C observed. Strength: Moderate.

*Peduncle*.—Length: 10 to 2 cm. Diameter: 3 to 5 mm. Color: Yellow-Green Group 144B. Texture: Smooth.

Flower bud development: Flower buds are borne in panicle like clusters of 15 flower buds on each peduncle. On average, each flowering branch bears 10 to 15 peduncles.

Flower bloom:

*Fragrance*.—Light.

*Duration*.—The blooms have a duration on the plant of approximately 7 to 10 days. Petals fall cleanly away from plant after flowers have fully matured.

*Size*.—Flower diameter is 50 mm when open. Flower depth is 15 mm.

*Flower shape*.—General shape is a an open cup with petals that curve out from the center.

*Shape of flower, side view*.—The upper portion is flat. The lower portion is concave.

Petalage: Under normal conditions, flowers have 20 petals total.

General tonality of flower: Open flowers are Red Group 46A. Tonality remains as the flower ages.

Petal color:

*Upon opening*.—Upper surface: Red Group 46A. Lower surface: Red-Purple Group 60A. Occasional streaks the color of White Group N155A.

*Basal petal spots, upon opening*.—Upper surface: Yellow Group 8B. Lower surface: Yellow Group 8B.

*After opening*.—Upper surface: Red Group 46A. Lower surface: Red-Purple Group 58A.

*Basal petal spots, after opening*.—Upper surface: Yellow Group 4D. Lower surface: Yellow Group 4D.

Petals:

*Petal reflex*.—Flat.

*Margin*.—Entire and uniform. Undulations of margin absent.

*Shape*.—Narrow elliptic. Apex shape: Rounded. Base shape: Acute.

*Size*.—25 mm (l)×25 mm (w).

*Texture*.—Smooth.

*Thickness*.—Average.

Petaloids: None observed.

Reproductive organs:

*Pollen*.—None observed.

*Anthers*.—Size: 2 mm in length. Color: Yellow-Orange Group 14C. Quantity: 40 on average.

*Filaments*.—Color: Yellow Group 8A. Length: 5 mm.

*Pistils*.—Length: 3 mm. Quantity: 10 on average.

*Stigmas*.—Color: Green-Yellow Group 1C.

*Styles*.—Color: Green-Yellow Group 1C.

*Location of stigmas*.—Inferior in location relative to the length of the filaments and the height of the anthers.

*Hips*.—None Observed.

Plant

Plant growth: Bushy. Plants are 75 cm in height and 75 cm wide.

Stems:

*Color*.—Juvenile growth: Yellow-Green Group 144B. Mature growth: Yellow-Green Group 146C.

*Length*.—On average, canes are 40 cm from the base of the plant to the flowering portion.

*Diameter*.—11 mm.

*Internodes*.—On mature canes 15 to 35 mm between nodes.

*Surface texture*.—Young wood: Smooth. Older wood: Smooth.

Long prickles:

*Incidence*.—13 prickles per 10 cm of stem.

*Size*.—Average length of prickles on mature stems is 12 mm.

*Shape*.—Upper portion is linear. Lower portion is deep concave.

*Color*.—Juvenile prickles: Greyed-Red Group 180A. Mature prickles: Greyed-Orange Group 164C.

Plant foliage:

*Compound leaf*.—160 mm (l)×90 (w).

*Quantity*.—3 leaves per 10 cm of stem on average.

*Leaf bearing angle to the stem*.—45 degrees.

*Color of mature foliage*.—Upper side: Yellow-Green Group 146A. Lower side: Yellow-Green Group 148C.

Plant leaves and leaflets:

*Stipules*.—Size: 25 mm in length. Quantity: 2 per compound leaf. Shape: Linear, slightly broad based with outward extending apecies. Margins: Deeply serrated with stipitate glands. Color: Green Group 143B.

*Petiole*.—Length: 30 mm. Diameter: 2.5 mm.

*Upper surface*.—Color: Yellow-Green Group 144D. Light intonations of Greyed-Red Group 178A. Observations: Stipitate glands.

*Lower surface*.—Color: Yellow-Green Group 144C. Observations: Small prickles.

*Rachis*.—Length: 70 mm on average. Color: Upper surface is Yellow-Green Group 144D. Light intonations of Greyed-Red Group 178A. Observations: Stipitate glands.

*Lower surface of rachis*.—Lower surface: Color: Yellow-Green Group 144C. Observations: Small prickles.

*Leaflet*.—Quantity: Normal number of leaflets leaves in middle of the stem is 5 to 7 leaflets. Margins: Serrated. Size: Average size of the terminal leaflet on normal leaves is 45 mm in length by 32 mm wide. Shape: Generally ovate. Base: Rounded. Apex: Mucronate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Ground Cover rose class named 'Poultc018', substantially as illustrated and described herein, due to its abundant red flowers, disease resistance, and extended period of bloom.

* * * * *